(12) United States Patent
Logan

(10) Patent No.: US 8,114,133 B2
(45) Date of Patent: Feb. 14, 2012

(54) SPINAL ROD SYSTEM

(76) Inventor: Joseph Nicholas Logan, Trumbull, CT (US)

( * ) Notice: Subject to any disclaimer, the term of this patent is extended or adjusted under 35 U.S.C. 154(b) by 1304 days.

(21) Appl. No.: 11/736,975

(22) Filed: Apr. 18, 2007

(65) Prior Publication Data

US 2007/0288011 A1    Dec. 13, 2007

Related U.S. Application Data

(60) Provisional application No. 60/792,931, filed on Apr. 18, 2006.

(51) Int. Cl.
*A61B 17/70* (2006.01)
(52) U.S. Cl. ........................................ 606/258
(58) Field of Classification Search ............... 606/246, 606/248, 251–260, 263
See application file for complete search history.

(56) References Cited

U.S. PATENT DOCUMENTS

| | | | |
|---|---|---|---|
| 4,946,458 A | 8/1990 | Harms et al. |
| 5,261,909 A | 11/1993 | Sutterlin et al. |
| 5,275,600 A | 1/1994 | Allard et al. |
| 5,282,863 A | 2/1994 | Burton |
| 5,318,566 A | 6/1994 | Miller |
| 5,360,431 A | 11/1994 | Puno et al. |
| 5,395,374 A | 3/1995 | Miller et al. |
| 5,443,467 A | 8/1995 | Biedermann et al. |
| 5,466,237 A | 11/1995 | Byrd, III et al. |
| 5,474,555 A | 12/1995 | Puno et al. |
| 5,476,462 A | 12/1995 | Allard et al. |
| 5,496,318 A | 3/1996 | Howland et al. |
| 5,496,322 A | 3/1996 | Mathews |
| 5,540,688 A | 7/1996 | Navas |
| 5,549,607 A | 8/1996 | Olson et al. |
| 5,672,175 A | 9/1997 | Martin |
| 5,688,272 A | 11/1997 | Montague et al. |
| 5,688,275 A | 11/1997 | Koros et al. |
| 5,702,394 A | 12/1997 | Henry et al. |
| 5,741,254 A | 4/1998 | Henry et al. |
| 5,797,911 A | 8/1998 | Sherman et al. |
| 5,836,948 A | 11/1998 | Zucherman et al. |
| 5,879,350 A | 3/1999 | Sherman et al. |
| RE36,221 E | 6/1999 | Breard et al. |
| 5,961,516 A | 10/1999 | Graf |
| 6,022,350 A | 2/2000 | Ganem |
| 6,053,917 A | 4/2000 | Sherman et al. |
| 6,068,630 A | 5/2000 | Zucherman et al. |
| 6,156,038 A | 12/2000 | Zucherman et al. |

(Continued)

OTHER PUBLICATIONS

International Search Report, PCT/US07/09417, Mar. 28, 2008, 2 pages.

*Primary Examiner* — Eduardo C Robert
*Assistant Examiner* — Tara Carter
(74) *Attorney, Agent, or Firm* — St. Onge Steward Johnston & Reens LLC

(57) ABSTRACT

A multi-axis spinal fixation device which can use a fixed head spinal or pedicle screw in combination with a multi-axial rod assembly to achieve anatomically correct fixation of vertebrae. The orthopedic fixation can be controlled by a different combination of rod elements to provide a varied range of motion between adjacent vertebrae as well as specific flexibility between the adjacent vertebrae or levels. The surgeon can make intra-operative adjustments from rigid fixation to dynamic stabilization and where desired also provide 'soft-stabilization' or 'micro motion'. The unique combination of elements can provide fixed stabilization for the purpose of fusion or dynamic stabilization without fusion.

38 Claims, 15 Drawing Sheets

U.S. PATENT DOCUMENTS

| | | |
|---|---|---|
| 6,183,471 B1 | 2/2001 | Zucherman et al. |
| 6,190,387 B1 | 2/2001 | Zucherman et al. |
| 6,193,720 B1 | 2/2001 | Yuan et al. |
| 6,235,030 B1 | 5/2001 | Zucherman et al. |
| 6,238,397 B1 | 5/2001 | Zucherman et al. |
| 6,261,287 B1 | 7/2001 | Metz-Stavenhagen |
| 6,267,764 B1 | 7/2001 | Elberg |
| 6,280,444 B1 | 8/2001 | Zucherman et al. |
| 6,332,883 B1 | 12/2001 | Zucherman et al. |
| 6,478,796 B2 | 11/2002 | Zucherman et al. |
| 6,500,178 B2 | 12/2002 | Zucherman et al. |
| 6,514,256 B2 | 2/2003 | Zucherman et al. |
| 6,537,276 B2 | 3/2003 | Metz-Stavenhagen |
| 6,569,164 B1 | 5/2003 | Assaker et al. |
| 6,582,433 B2 | 6/2003 | Yun |
| 6,585,738 B1 | 7/2003 | Mangione et al. |
| 6,616,669 B2 | 9/2003 | Ogilvie et al. |
| 6,626,904 B1 | 9/2003 | Jammet et al. |
| 6,626,944 B1 | 9/2003 | Taylor |
| 6,652,527 B2 | 11/2003 | Zucherman et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,736,817 B2 | 5/2004 | Troxell et al. |
| 6,743,231 B1 | 6/2004 | Gray et al. |
| 6,770,075 B2 | 8/2004 | Howland |
| 6,802,844 B2 | 10/2004 | Ferree |
| 6,852,128 B2 | 2/2005 | Lange |
| 6,858,030 B2 | 2/2005 | Martin et al. |
| 6,964,667 B2 | 11/2005 | Shaolian et al. |
| 6,966,910 B2 | 11/2005 | Ritland |
| 6,974,460 B2 | 12/2005 | Carbone et al. |
| 6,989,011 B2 | 1/2006 | Paul et al. |
| 6,991,632 B2 | 1/2006 | Ritland |
| 7,008,424 B2 | 3/2006 | Teitelbaum |
| 7,011,660 B2 | 3/2006 | Sherman et al. |
| 2002/0007183 A1 | 1/2002 | Lee et al. |
| 2003/0083657 A1 | 5/2003 | Drewry et al. |
| 2003/0105460 A1 | 6/2003 | Crandall et al. |
| 2004/0039387 A1 | 2/2004 | Gause et al. |
| 2004/0049190 A1 | 3/2004 | Biedermann et al. |
| 2004/0138666 A1 | 7/2004 | Molz, IV et al. |
| 2004/0143264 A1 | 7/2004 | McAfee |
| 2004/0260283 A1 | 12/2004 | Wu et al. |
| 2005/0033295 A1 | 2/2005 | Wisnewski |
| 2005/0038432 A1* | 2/2005 | Shaolian et al. ............ 606/61 |
| 2005/0055096 A1 | 3/2005 | Serhan et al. |
| 2005/0065516 A1 | 3/2005 | Jahng et al. |
| 2005/0124991 A1* | 6/2005 | Jahng ............ 606/61 |
| 2005/0125063 A1 | 6/2005 | Matge et al. |
| 2005/0131407 A1* | 6/2005 | Sicvol et al. ............ 606/61 |
| 2005/0143737 A1 | 6/2005 | Pafford et al. |
| 2005/0149020 A1* | 7/2005 | Jahng ............ 606/61 |
| 2005/0177157 A1 | 8/2005 | Jahng |
| 2005/0203509 A1 | 9/2005 | Chinnaian et al. |
| 2005/0228501 A1 | 10/2005 | Miller et al. |
| 2005/0277924 A1 | 12/2005 | Roychowdhury |
| 2006/0009766 A1 | 1/2006 | Lee et al. |
| 2006/0036240 A1 | 2/2006 | Colleran et al. |
| 2006/0036244 A1 | 2/2006 | Spitler et al. |
| 2006/0036252 A1 | 2/2006 | Baynham et al. |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0041259 A1 | 2/2006 | Paul et al. |
| 2006/0052783 A1 | 3/2006 | Dant et al. |
| 2006/0052784 A1 | 3/2006 | Dant et al. |
| 2006/0052785 A1 | 3/2006 | Augostino et al. |
| 2006/0058787 A1 | 3/2006 | David |
| 2006/0058800 A1 | 3/2006 | Ainsworth et al. |

* cited by examiner

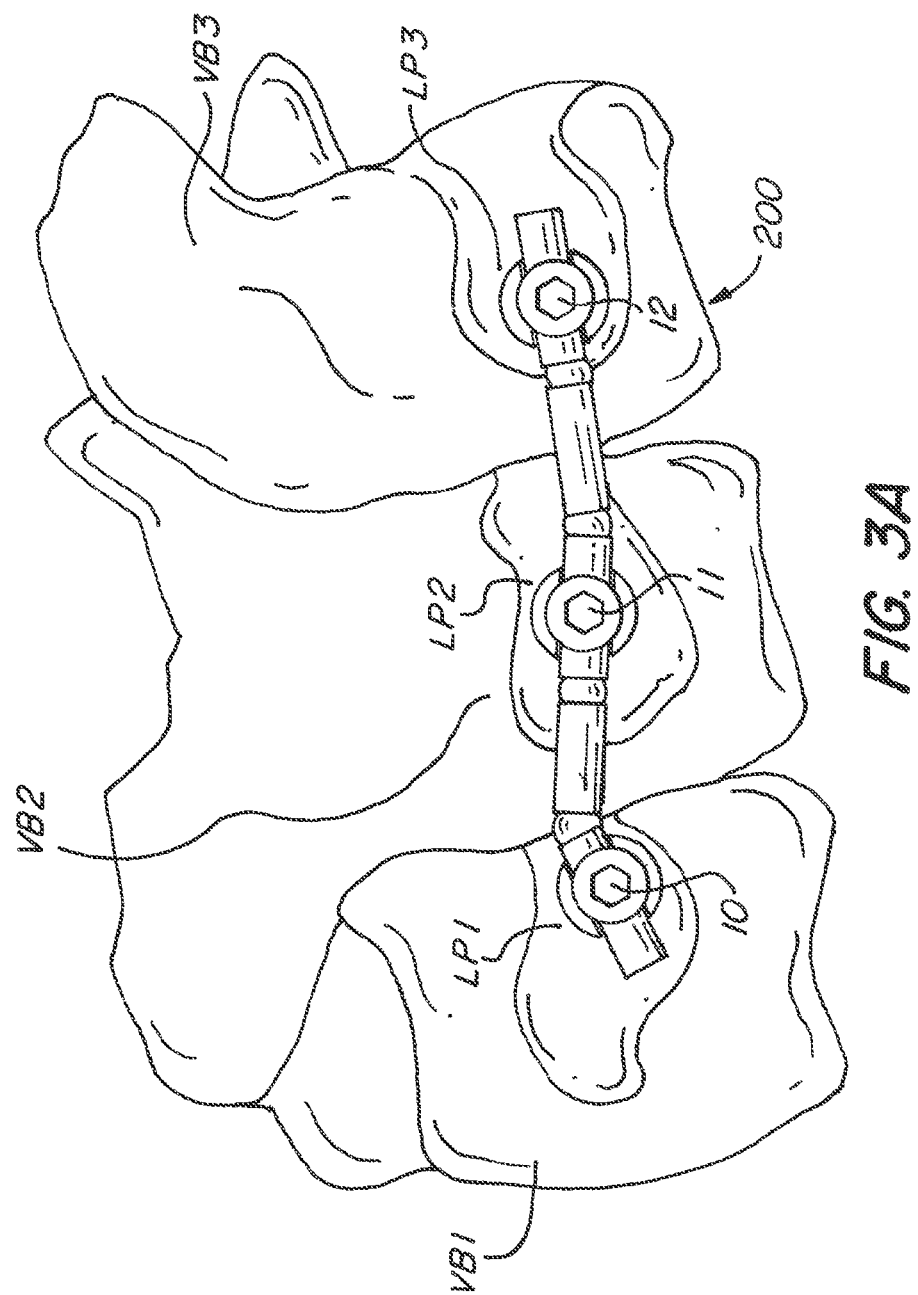

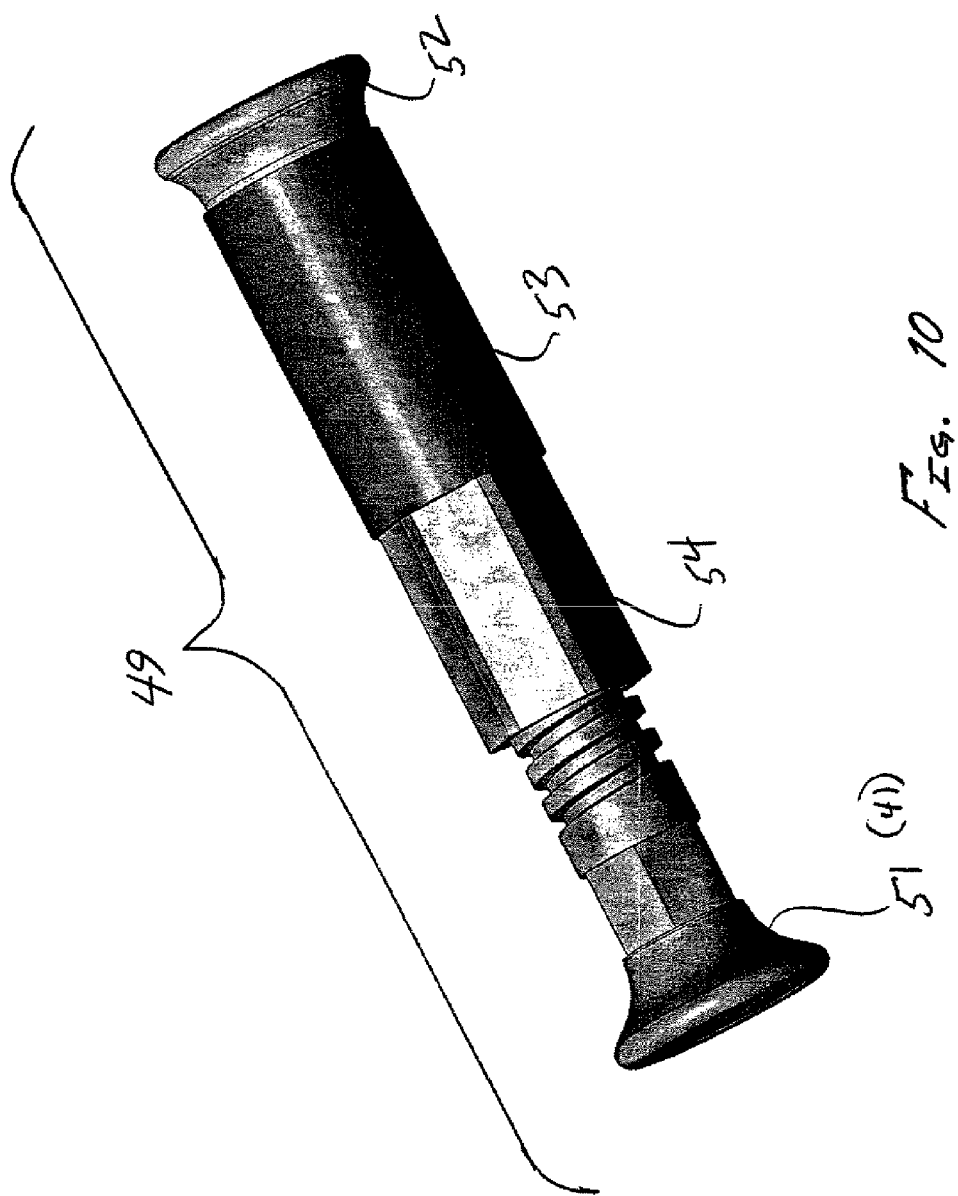

SPINAL ROD SYSTEM

CROSS REFERENCE TO RELATED APPLICATIONS

The present application claims the benefit of priority under 35 U.S.C. §119(e) to U.S. Provisional Application No. 60/792,931 filed on Apr. 18, 2006, entitled "Spinal Rod System," the entirety of which is incorporated by reference herein.

FIELD OF THE INVENTION

This invention relates generally to orthopedic stabilization devices and, more particularly, to a multi-axis spine stabilization system for securing vertebrae together for the purpose of fusion or dynamic stabilization without fusion.

BACKGROUND OF THE INVENTION

The use of fixation devices for the treatment of degenerative disc disease, vertebrae and spinal deformities and trauma is well known in the art. U.S. Pat. No. 6,966,910 to Ritland and U.S. Patent Application Publication No. 20050177157 of Jahng thoroughly describe the state of the art, the disclosures of which are incorporated by reference herein. In general, spinal column diseases often require surgical treatment when more conservative management and treatment is unsuccessful. Such surgical treatments are often directed to reducing pressure on nerve roots in the spinal canal or to addressing instability in the spine. Reducing pressure on nerve roots in the spinal canal typically involves spinal decompression which involves the removal of certain tissue from the spinal column. This removal of tissue weakens the spinal column.

Spinal fusion is sometimes used to provide stability to the spine. Spinal fusion is the technique of combining two or more vertebrae using supplementary bone tissue and the human body's natural osteoblastic processes. Spinal fusion prevents relative movement between the fused vertebrae to alleviate pain and injury associated with such movement.

In some cases, spinal fixation is used in conjunction with spinal fusion due to the time which is sometimes required for spinal fusion to provide adequate stability. Spinal fixation refers to the use of rods or plates attached to selected vertebrae by fixing screws so as to hold that portion of the spine in a relatively fixed position. The devices used, i.e. the rods, plates, and screws, are eventually removed from the patient once an adequate amount of spine healing and stability is achieved. Traditional spinal fixation is often referred to as "rigid fixation" because there is little to no movement of the relevant portion of the spine while the fixation devices are in place.

As is also well known in the art, there are serious drawbacks to spinal fusion and spinal fixation techniques. Most prominently, when a small part of the spine is immobilized, the movement of other adjacent parts of the spine is increased in response to the patient's normal movements. The increased movement by parts of the spine adjacent to immobilized vertebrae causes significant strain and wear on those adjacent parts. Such strain could lead to further injury and pain.

As a result, other techniques are sometimes employed for supporting the spine. Dynamic fixation refers to the use of spinal fixation devices which are not completely rigid but which have a selected amount of flex to allow an appropriate amount of movement of the relevant portions of the spine. Such movement has been determined to be beneficial in some cases in aiding a patient's recovery from spinal injury and/or surgery. Many dynamic fixation devices and techniques are disclosed in the prior art.

One type of dynamic fixation system involves using flexible members secured by bone anchors which are attached to a patient's vertebrae. For example, U.S. Pat. No. 6,966,910 to Ritland discloses a dynamic fixation device and a method for its use. The device comprises a flexible rod portion attached to pedicle screws, where the screws are inserted into the vertebrae of the spine. The flexible rod portion is made of elastomeric material or an alloy appropriately shaped to function as a spring and/or pivot. The device allows for limited motion which models the bending motion of the spine.

U.S. Patent Application Publication No. 2005/0177157 of Jahng discloses a method and apparatus for flexible fixation of a spine. The apparatus comprises at least one flexible fixation rod secured to a patient's spinal pedicles by screw-type members. A flexible wire is sometime used, which traverses an axial cavity of the rod members, to connect multiple rod members together. The screw-type members use a cylindrical head, a screw-type shaft, and an outside threaded nut to clamp onto the rod members and screw into the patient's bone tissue.

Many other devices have been used to achieve spine stabilization, whether fixed or dynamic. Unfortunately, these devices have serious drawbacks. One serious drawback is that it is often difficult to install the rod members in the bone anchors. The bone anchors often require that the rod member be installed with a particular orientation relative to the bone anchor. When the rod member is to be installed in more than one anchor, it can be difficult to orient the rod properly without damaging the rod, the bone anchors, or even the body tissues of the patient. The prior art fails to provide pedicle screw to rod connectors that can be easily adjusted at the time of implantation for off-axis, out of plane and non-linear alignment conditions. First positioning the bone screws in the vertebrae for proper holding strength and then trying to position the vertebrae and fit a straight rod or actually trying to bend a rod into the resulting multi-axial geometry at each rod screw head interface or coupling point is a daunting task.

There have also been many attempts to alleviate this difficulty. Most prominently, screws with multi-axial or poly-axial heads are used as bone anchors. A multi-axial head is designed to receive a rod member oriented at one of many different angles relative to the screw. Such a screw is disclosed in, for example, U.S. Pat. No. 5,797,911 to Sherman et. al and U.S. Patent Application Publication No. 2002/0026193 of Barker et al.

The use of pedicle screws with multi-axial or articulating heads to receive the connecting rods does alleviate some of the problems and difficulties in accurately bending the rods to fit the geometry but does not completely solve the problem. First, they are relatively difficult and time-consuming to properly install and adjust. Each screw is generally comprised of multiple components, each of which must be carefully set into the desired position. This further complicates the actual connection of the rod to the screw head in the adjacent vertebra. It can also cause further difficulties in making final adjustments to the relative position of vertebrae and the interbody space.

Articulating multi-axis screw heads are still cumbersome and alignment results can be poor. Potential damage to the screw and the rod can occur as a result of bending the components in place and this damage could cause premature failure of the fixation system or cause trauma to the vertebrae itself.

What is needed then is a spine stabilization system which is easy to properly install while still providing effective stabilization. The amount of flexibility in the system should be adjustable to allow for use with spine problems of various types. The system should be capable of fixed stabilization as well as varying degrees of dynamic stabilization. The system should also be simple and inexpensive to manufacture.

SUMMARY OF THE INVENTION

It is therefore an object of the present invention to provide a spine stabilization system which is simple to install without the risk of applying excessive force on the components of the system or the body tissues of the patient, but which still provides effective and adequate stabilization.

It is a further object of the present invention to provide a spine stabilization system the flexibility of which may be adjusted for use with spine problems of various types.

It is still a further object of the present invention to provide a spine stabilization system which functions as a fixed stabilization system or, alternatively, as a dynamic stabilization system with varying degrees of flexibility.

It is yet a further object of the present invention to provide a spine stabilization system which is simple and inexpensive to manufacture.

These and other objects are accomplished by the present invention according to one embodiment by provision of a spine stabilization system, which includes a rod assembly and at least two bone anchor assemblies. The rod assembly includes a plurality of rod members, each rod member having a length and comprising a first end and a second end, wherein each of the first end and the second end has a substantially round end surface, and each rod member has an axial channel along its length. The rod assembly also includes at least one substantially round pivot member which is disposed between rod members and which makes substantially flush contact with the round end surfaces of the rod members and which has a channel. The rod assembly also includes a tether disposed in the axial channels of the rod members and the channel of the at least one substantially round pivot member. Each bone anchor assembly includes an anchor member comprising a lower rod portion for insertion into bone tissue and an upper portion, wherein the upper portion is adapted to receive a portion of a rod member and has an inner threaded surface. Each bone anchor assembly also includes a screw top member having an outer threaded surface for engaging with the inner threaded surface of the upper portion of the anchor member. The bone anchor assemblies hold the rod assembly between the screw top member and the upper portion of the anchor member.

In some embodiments, the rod assembly also includes at least one adjustable rod member, which includes a first component comprising a first end with a substantially round end surface, a second end, an axial channel for receiving the tether, and threads on an outer surface of the first component adjacent to the second end; a second component comprising a first end, a second end with a substantially round end surface, an axial channel for receiving the tether, and threads adjacent to the first end on an inner surface of the axial channel; and wherein the threads of the first component engage with the threads of the second component such that the overall length of the adjustable rod member may be adjusted. In some embodiments, the second component further comprises an elastomeric element disposed between the first end and the second end of the second component.

In some embodiments, the spine stabilization system also includes at least one bone screw assembly. The bone screw assembly including: a screw shaft member comprising a lower portion for inserting into bone tissue and an upper rounded portion adapted to interface with the substantially round end surface of at least one rod member, and wherein the upper rounded portion has a threaded inner cylindrical surface; a screw head member receivable within the upper rounded portion of the screw shaft member, wherein the screw head member includes threads on an outer surface thereof designed to engage the threads on the inner cylindrical surface of the upper rounded portion of the screw shaft member; and wherein the at least one bone screw assembly is disposed at the end of at least one rod member of the rod assembly such that the tether may be anchored in place between the screw shaft member and the screw head member, thereby connecting the at least one bone screw assembly and the rod assembly.

In some embodiments, the screw head member includes a protrusion on its lower surface which pierces the tether. In some embodiments, the tether is formed of an elastomeric material. In some embodiments, the rod members having varying lengths. In some embodiments, the rod assembly includes at least one rod member comprising an elastomeric element disposed between the first end and the second end of the rod member. In some embodiments, the rod assembly includes tether anchor members for preventing movement of the tether relative to the other components of the rod assembly. In some embodiments, at least one substantially round pivot member is formed of an elastomeric material.

According to another embodiment of the present invention, a spine stabilization system is provided, which includes a rod assembly and at least two bone screw assemblies. The rod assembly includes at least one rod member having a length and comprising a first end and a second end, wherein at least one of the first end and the second end has a substantially round end surface, and the at least one rod member has an axial channel along its length. The rod assembly also includes a tether disposed in the axial channel. At least one of the bone screw assemblies includes a screw shaft member comprising a lower portion for inserting into bone tissue and an upper rounded portion adapted to interface with the substantially round end surface of the at least one rod member. Wherein the bone screw assemblies are disposed at the end of the at least one rod member of the rod assembly such that the tether connects the bone screw assemblies and the rod assembly.

In some embodiments, at least one of the bone screw assemblies also includes that the upper rounded portion of the screw shaft member has a threaded inner cylindrical surface and a screw head member receivable within the upper rounded portion of the screw shaft member, wherein the screw head member includes threads on an outer surface thereof designed to engage the threads on the inner cylindrical surface of the upper rounded portion of the screw shaft member; wherein the tether may be anchored in place between the screw shaft member and the screw head member. In some embodiments, the screw head member includes a protrusion on its lower surface which pierces the tether.

In some embodiments, the rod assembly further comprises at least one adjustable rod member, comprising: a first component comprising a first end with a substantially round end surface, a second end, an axial channel for receiving the tether, and threads on an outer surface of the first component adjacent to the second end; a second component comprising a first end, a second end with a substantially round end surface, an axial channel for receiving the tether, and threads adjacent to the first end on an inner surface of the axial channel; and wherein the threads of the first component engage with the threads of the second component such that the overall length of the adjustable rod member may be adjusted.

In some embodiments, the second component further comprises an elastomeric element disposed between the first end and the second end of the second component. In some embodiments, the tether is formed of an elastomeric material. In some embodiments, the rod assembly comprises a plurality of the rod members. In some embodiments, the rod members have varying lengths. In some embodiments, the rod assembly further comprises at least one substantially round pivot member which is disposed between rod members and has a channel in which the tether is disposed so as to connect the at least one substantially round pivot member with the rod members. In some embodiments, at least one of the substantially round pivot members is formed of an elastomeric material. In some embodiments, the spine stabilization system further comprises at least one bone anchor assembly which comprises an anchor member and a screw top member for attaching between the first end and the second end of a rod member. In some embodiments, the rod assembly includes at least one rod member comprising an elastomeric element disposed between the first end and the second end of the rod member.

According to another embodiment of the present invention, a spine stabilization system is provided, which includes a rod assembly and a plurality of bone screw assemblies. The rod assembly includes one or more elongated rod members wherein each elongated rod member comprises a channel extending along its longest dimension and a first end and a second end both having a substantially round end surface; at least one adjustable rod member; and a tether disposed in the channels of the elongated rod members and the adjustable rod members and linking the elongated rod members and the adjustable rod members together. An adjustable rod member comprises: a first component comprising a first end with a substantially round end surface, a second end, an axial channel, and threads on an outer surface of the first component adjacent to the second end; a second component comprising a first end, a second end with a substantially round end surface, an axial channel, and threads adjacent to the first end on an inner surface of the axial channel; and wherein the threads of the first component engage with the threads of the second component such that the overall length of the adjustable rod member may be adjusted. The bone screw assemblies are disposed between the elongated rod members and the adjustable rod members of the rod assembly. At least one bone screw assembly comprises a screw shaft member comprising a lower portion for inserting into bone tissue and an upper rounded portion adapted to interface with the substantially round end surfaces of the elongated rod members and the adjustable rod members.

In some embodiments, at least one bone screw assembly further comprises: that the upper rounded portion of the screw shaft member has a threaded inner cylindrical surface; and a screw head member receivable in the upper rounded portion of the screw shaft member, comprising a threaded outer surface for engaging with the threaded inner cylindrical surface of the upper rounded portion and which contacts the tether of the rod assembly to substantially prevent movement of the tether relative to the bone screw assembly.

In some embodiments, the screw head member has a protrusion on a lower surface which pierces the tether. In some embodiments, the tether is formed of an elastomeric material. In some embodiments, at least one second component of the at least one adjustable rod member further comprises an elastomeric element disposed between the first end and the second end of the second component. In some embodiments, the rod assembly comprises a plurality of the elongated rod members. In some embodiments, the elongated rod members have varying lengths. In some embodiments, the rod assembly further comprises at least one substantially round pivot member which is disposed between the elongated rod members and the adjustable rod members and has a channel in which the tether is disposed so as to connect the substantially round pivot members with the elongated rod members and the adjustable rod members. In some embodiments, at least one substantially round pivot member is formed of an elastomeric material. In some embodiments, the spine stabilization system further comprises at least one bone anchor assembly which comprises an anchor member and a screw top member for attaching between the first end and the second end of an elongated rod member.

According to yet another embodiment of the present invention, a spine stabilization system is provided, which includes a rod assembly and at least two bone anchor assemblies. The rod assembly includes a plurality of adjustable rod members. Each adjustable rod member comprises a first component comprising a first end with a substantially round end surface, a second end, an axial channel, and threads on an outer surface of the first component adjacent to the second end; a second component comprising a first end, a second end with a substantially round end surface, an axial channel, and threads adjacent to the first end on an inner surface of the axial channel; and wherein the threads of the first component engage with the threads of the second component such that the overall length of the adjustable rod member may be adjusted. The rod assembly also includes at least one substantially round pivot member having a channel and being disposed between two adjustable rod members such that an outer surface of the at least one substantially round pivot member is in substantially flush contact with the substantially rounded end surfaces of the adjustable rod members and such that the channel of the at least one substantially round pivot member is aligned with the axial channels of the adjustable rod members. The rod assembly also includes a tether passing through the channels of the at least one pivot member and the axial channels of the adjustable rod members. Each bone anchor assembly comprises an anchor member comprising a lower rod portion for insertion into bone tissue and an upper portion, wherein the upper portion is adapted to receive a portion of a rod member and has an inner threaded surface; and a screw top member having an outer threaded surface for engaging with the inner threaded surface of the upper portion of the anchor member. Wherein the rod assembly is secured between the anchor members and the screw top members of the bone anchor assemblies.

In some embodiments, the tether is formed of an elastomeric material. In some embodiments, at least one substantially round pivot member is formed of an elastomeric material. In some embodiments, the spine stabilization system further comprises at least one bone screw assembly, comprising: a screw shaft member comprising a lower portion for inserting into bone tissue and an upper rounded portion adapted to interface with the substantially round end surface of at least one adjustable rod member, and wherein the upper rounded portion has a threaded inner cylindrical surface; a screw head member receivable within the upper rounded portion of the screw shaft member, wherein the screw head member includes threads on an outer surface thereof designed to engage the threads on the inner cylindrical surface of the upper rounded portion of the screw shaft member; wherein the at least one bone screw assembly is disposed at the end of at least one adjustable rod member of the rod assembly such that the tether may be anchored in place between the screw shaft member and the screw head member, thereby connecting the at least one bone screw assembly and the rod assembly. In some embodiments, at least one second component of an adjustable rod member further comprises an elastomeric element disposed between the first end and the second end of the second component.

According to another embodiment of the present invention, an adjustable rod member for use in a spine stabilization system is provided, comprising: a first component comprising a first end with a substantially round end surface, a second end, an axial channel, and threads on an outer surface of the first component adjacent to the second end; a second component comprising a first end, a second end with a substantially round end surface, an axial channel, an elastomeric element disposed between the first end and the second end, and threads adjacent to the first end on an inner surface of the axial channel; and wherein the threads of the first component engage with the threads of the second component such that the overall length of the adjustable rod member may be adjusted.

The system provides a spinal fixation device that can be controlled by a different combination of rod elements to provide a varied range of motion between adjacent vertebrae as well as specific flexibility between adjacent vertebrae or spine levels. The surgeon can make intra-operative adjustments from rigid fixation to dynamic stabilization and where desired also provide 'soft-stabilization' or 'micro motion'. The unique combination of elements can provide fixed stabilization for the purpose of fusion or dynamic stabilization without fusion.

The system can be configured for use as a: (1a) rigid fixed system between one or more pairs of adjacent vertebrae that provides for fusion, or (1b) a rigid but not totally fixed system between one or more pairs of adjacent vertebrae that provides for a slight degree of movement or 'micro motion' in the intervertebral space, or (2) a flexible or dynamic system between one or more pairs of adjacent vertebrae to provide a controlled range of motion and controlled flexion and extension reaction forces, or (3) a combination of (1a) and/or (1b) and/or (2) between two or more pairs of vertebrae, or (4) the further use of the hybrid dynamic stabilization system in (3) above with other arthoplasty devices (such as prosthetic discs, the spinous process or vertebral pedicles) used in spinal stabilization and in the treatment of degenerative disc disease.

The rigid fixed system provides mechanical simplicity and the ease and accuracy of positioning of the rod members in the anchoring pedicle screws in the vertebrae. An advantage is that there is no forcing or bending of the rod to fit the screw head. This eliminates the possibility of damaging or compromising the mechanical integrity of the rod, screw or even the vertebrae. The means of connecting the rods to provide for multi-axial and multi-plane positioning to the pedicle screws does not require an intricate articulating head for alignment. The invention uses fixed head screws (a standard female yoke in one configuration or a male ball for coupling of a rod end with a female receiving spherical radius in an alternate embodiment).

The rigid fixed system utilizes a "configurable" rod assembly that has pivoting or articulating points in the rod assembly itself. The actual connection of the rod to the screw head is always in-line or in plane and on axis by virtue of the fact that the section of the rod that mates with the screw head is free to align with its' mating screw geometry. After the rod freely takes the position through the screw heads it is locked into position by securing the ends of the tensioned tether. The tether may in turn be locked to each screw assembly by a screw head that holds the tether by compression and also by means of a small protrusion at the crown that pierces the tether to further lock it from slipping or moving between any of the screw assemblies.

Alternatively, the articulating points are achieved in the regions associated with the head of the screw assembly. Such articulation is achieved by a rod member that couples adjacent screw assemblies and has substantially round end surfaces of the rod that receive substantially round surfaces formed at the heads of adjacent screw assemblies. Such an embodiment is further improved if the rod has an adjustable length capability.

This system also provides for dynamic stabilization by incorporating an elastomeric element in a rod member or a component of the rod member. The elastomeric element is incorporated in a component of a rod member and can be shaped such that it is integrated into the body of the rod member. In such a case, it is beneficial if the core of the elastomeric component has a channel that aligns with the channel formed in the overall rod member.

Other objects of the invention and its particular features and advantages will become more apparent from consideration of the following drawings and accompanying description.

BRIEF DESCRIPTION OF THE DRAWINGS

FIG. 3A is a posterior perspective view of one of the spine stabilization systems of FIG. 1.

FIG. 10 is a perspective view of an adjustable rod member with an elastomeric element of a rod assembly of the spine stabilization system of FIG. 8.

DETAILED DESCRIPTION OF THE INVENTION

Figure 1:
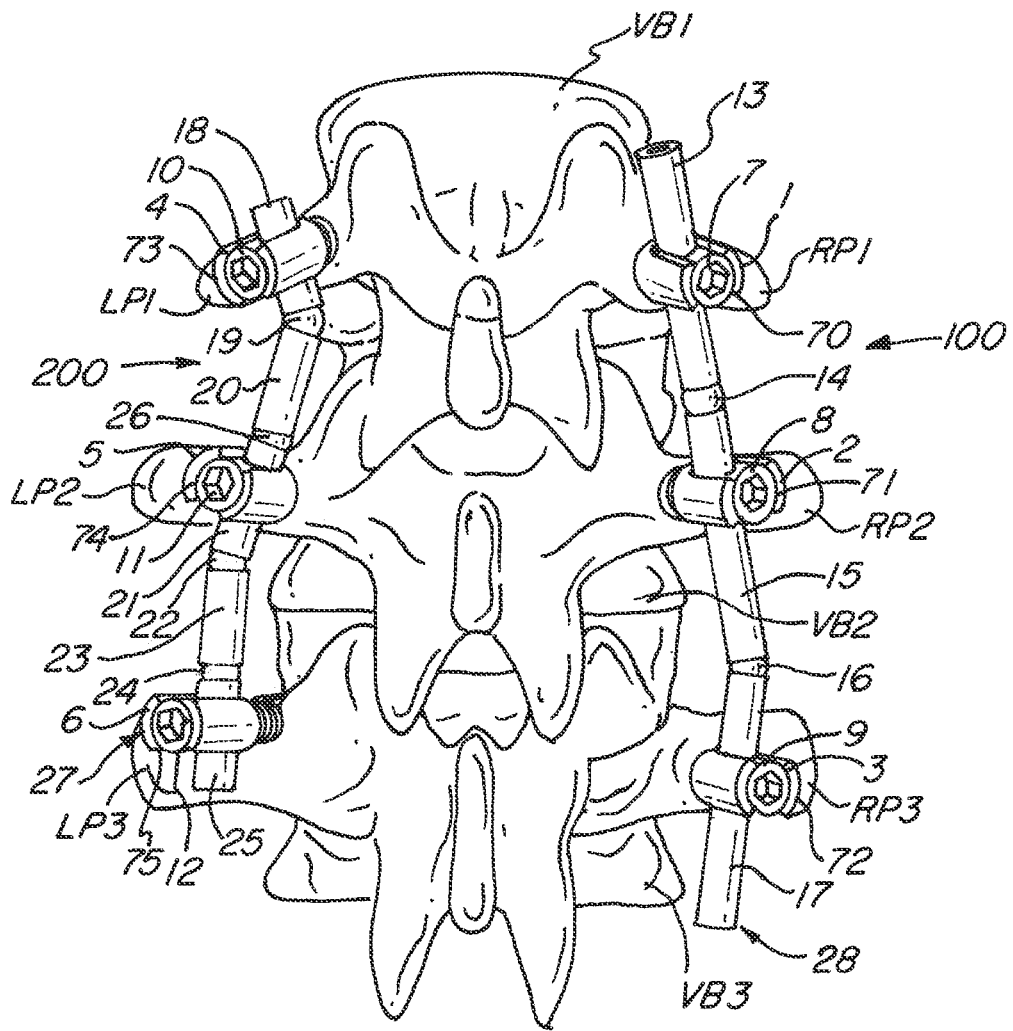
FIG. 1 is a posterior view of a spine stabilization system according to the present invention installed in three spine vertebrae (and across two motion segments).

Embodiments of the present invention will now be described with reference to the accompanying drawings. FIG. 1 shows spine stabilization systems according to the present invention installed in three vertebrae of a human spine. The systems shown in FIG. 1 are rigid fixation systems which permit little to no relative movement between the relevant vertebrae. The three vertebrae VB1, VB2, and VB3 have left pedicles LP1, LP2, and LP3 and right pedicles RP1, RP2, and RP3. Spine stabilization systems 100 and 200 include the rod assemblies 27 and 28 and are secured to vertebrae VB1, VB2, and VB3 by bone anchor assemblies 70, 71, 72, 73, 74, and 75. Rod assemblies 27 and 28 are made up of rod members 13, 15, 17, 18, 20, 21, 23, and 25, pivot members 14, 16, 19, 26, 22, and 24, and a tether (not shown in FIG. 1) in each of rod assemblies 27 and 28. The bone anchor assemblies 70, 71, 72, 73, 74, and 75 comprise anchor members 1, 2, 3, 4, 5, and 6 and screw top members 7, 8, 9, 10, 11, and 12. The anchor members 1, 2, 3, 4, 5, and 6 are anchored to the vertebrae and the screw top members 7, 8, 9, 10, 11, and 12 secure the rod assemblies 27 and 28 to the anchor members. While these systems can be used with bone screws that have fixed heads or articulating heads, the embodiments shown in FIG. 1 use fixed head anchors.

FIGS. 1, 2, 3A, and 3B show three vertebrae, but it should be understood that the present invention is advantageously employed on two or more vertebrae as needed. The number of vertebrae on which the present invention is to be employed varies according to the particular case and patient.

Figure 2:
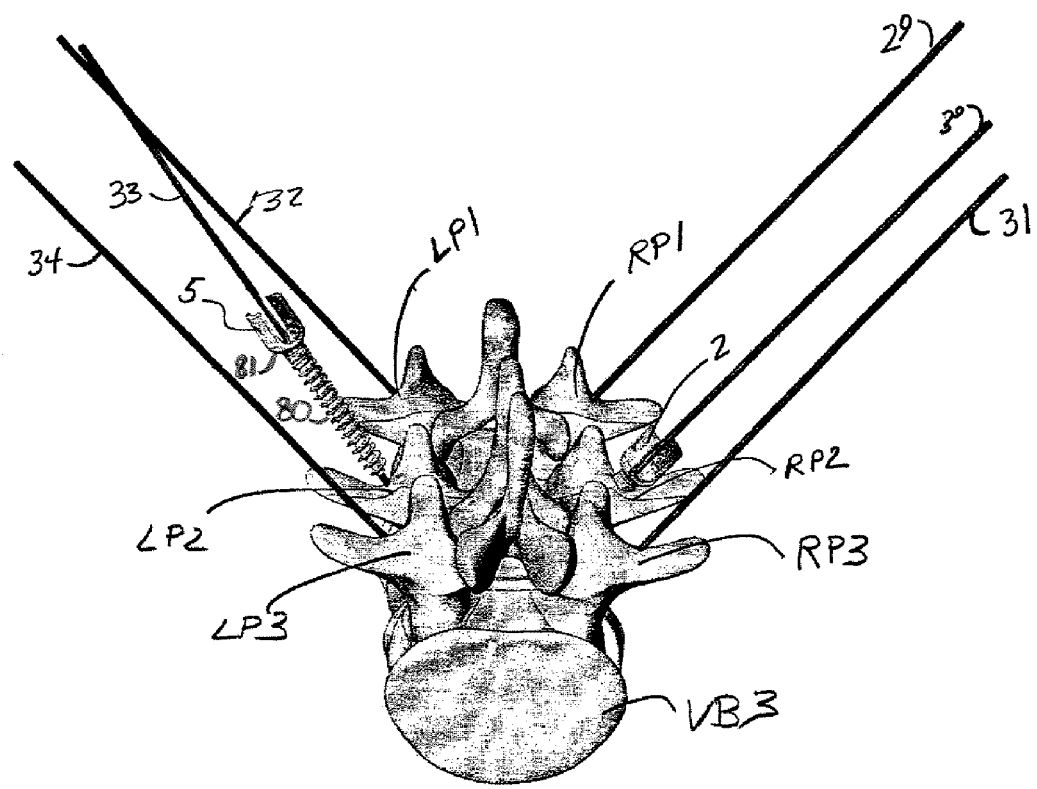
FIG. 2 is an axial view of the vertebrae of FIG. 1 showing the placement of guide wires and pedicle screws in vertebral bodies.

FIG. 2 shows the spine section of FIG. 1 at a different angle. FIG. 2 shows guide wires representing the angles of insertion 29, 30, 31, 32, 33, and 34 of the anchor members into left pedicles LP1, LP2, and LP3 and right pedicles RP1, RP2, and RP3. Anchor members 2 and 5 are shown in different stages of insertion. Anchor member 5, which is exemplary of anchor members 1, 2, 3, 4, 5, and 6 of the embodiment shown in FIG. 1, has a lower rod portion 80 which has threads for anchoring the member in bone tissue and an upper portion 81.

Figure 3B:
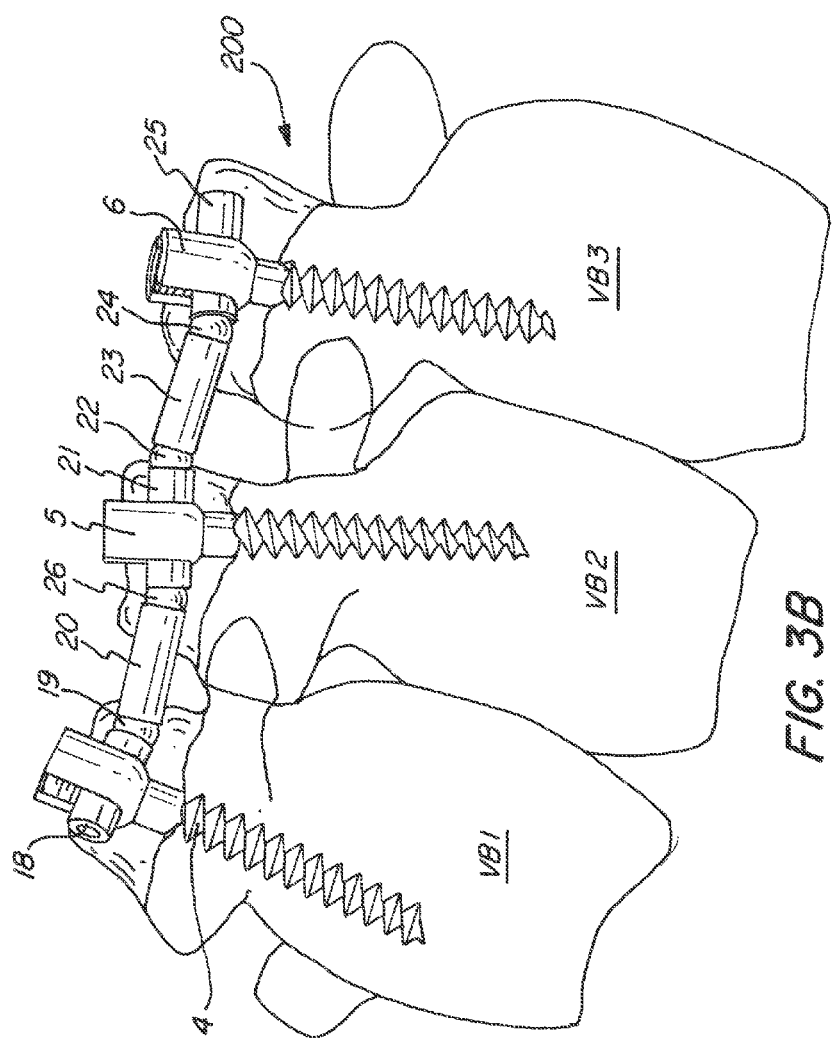
FIG. 3B is a lateral view of one of the spine stabilization systems of FIG. 1.

FIGS. 3A and 3B show alternate views of the spinal stabilization system 200 of FIG. 1. In these figures, the bone tissue of vertebrae VB1, VB2, and VB3 is depicted as semi-transparent to show the anchor members 4, 5, and 6. Because the rod members 13, 15, 17, 18, 20, 21, 23, and 25 may articulate relative to one another about the pivot members 14, 16, 19, 26, 22, and 24, each rod member may be of adequately aligned or oriented and secured to an anchor member without the need of excessive force applied to the anchor members or the vertebrae. Articulation within a rod assembly according to the present invention is described in more detail below.

Figure 4:
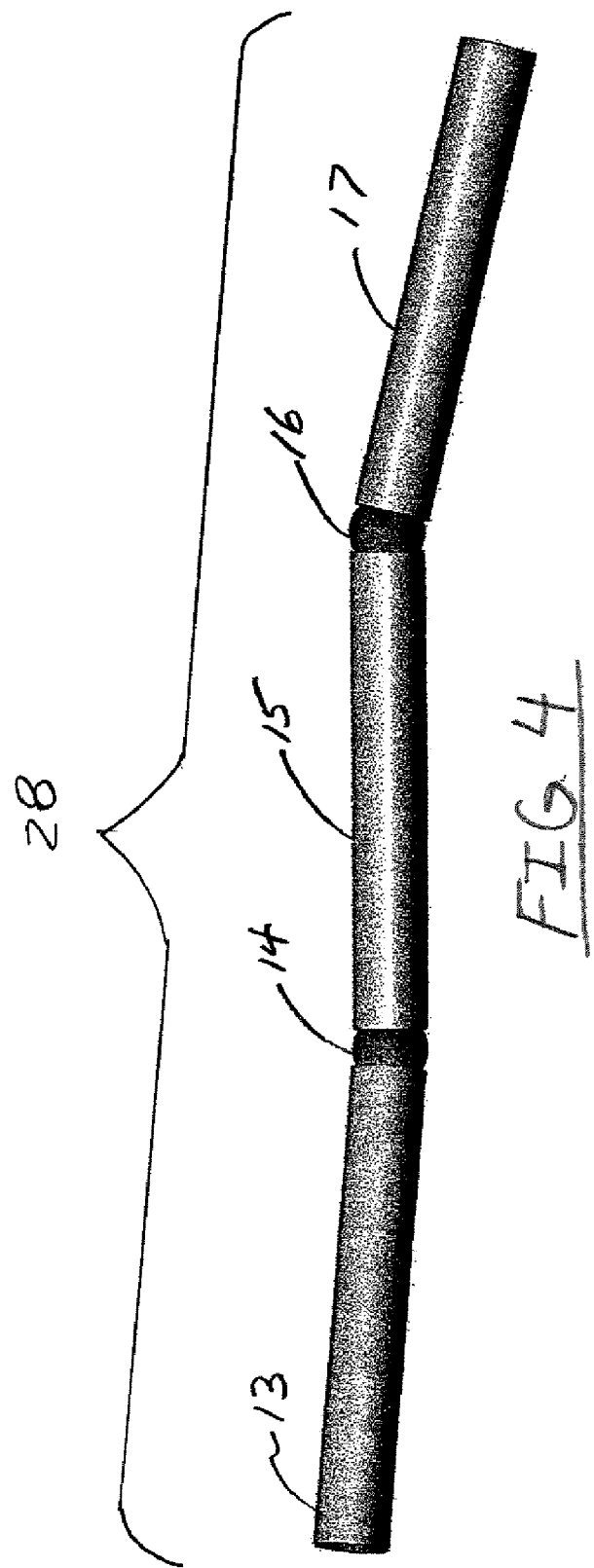
FIG. 4 is a perspective view of a rod assembly of one of the spine stabilization systems of FIG. 1.

FIG. 4 shows a close up view of rod assembly 28 with rod members 13, 15, and 17 and pivot members 14 and 16. The pivot members 14 and 16 are substantially round in shape and interface with the end surfaces of the rod members 13, 15, and 17. The end surfaces of the rod members 13, 15, and 17 are also substantially round shaped such that the surfaces of the pivot members and the rod members substantially correspond and mate together. When the spine stabilization system is installed, the pivot members and the rod members make substantially flush contact at their substantially round surfaces. As a result of the fact that both the pivot members and the end surfaces of the rod members are substantially round, the rod members are capable of articulation relative to one another about the pivot members. This makes the process of installation of the spine stabilization system significantly easier.

In the current embodiment, the rod members 13, 15, and 17 are formed of a rigid, non-elastic material, such as metal, alloy, ceramic, hard plastic, or the like. In some embodiments, when rigid fixation is desired, the pivot members according to the present invention are also formed of a rigid, non-elastic material, such as metal, alloy, ceramic, hard plastic, or the like. In other embodiments, however, pivot members according to the present invention are formed of an elastomeric material to provide the spine stabilization system the capability of a small amount of movement. In other embodiments, the pivot members comprise a rigid core surrounded by an elastomeric surface. In such situations, the spine stabilization system is sometimes described as having 'micro-motion' or 'soft-stabilization.' In some cases, 'micro-motion' or 'soft-stabilization' is considered to facilitate patient healing.

Figure 4A:
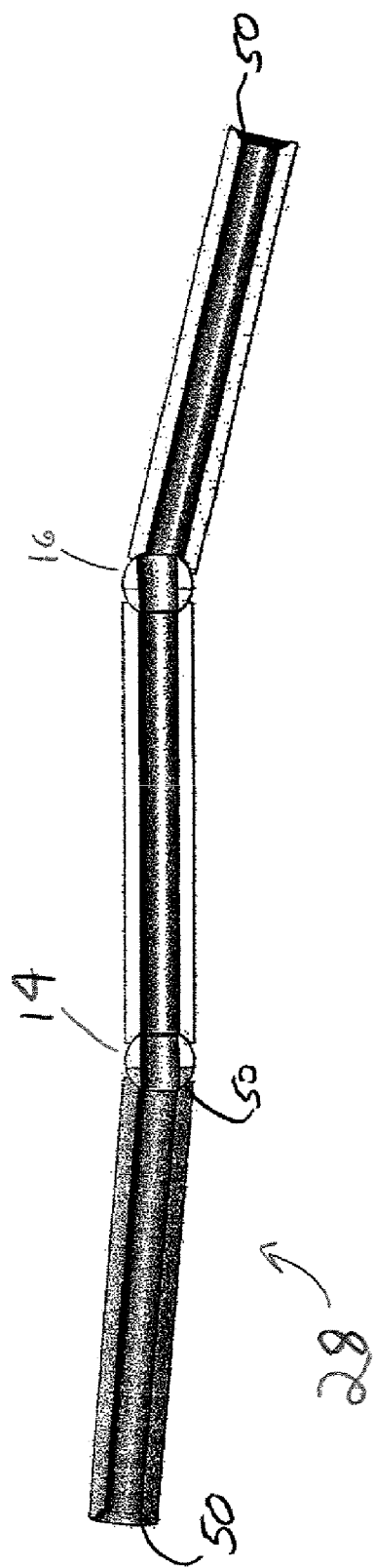
FIG. 4A is a cross-section view of the rod assembly of FIG. 4.
Figure 7:
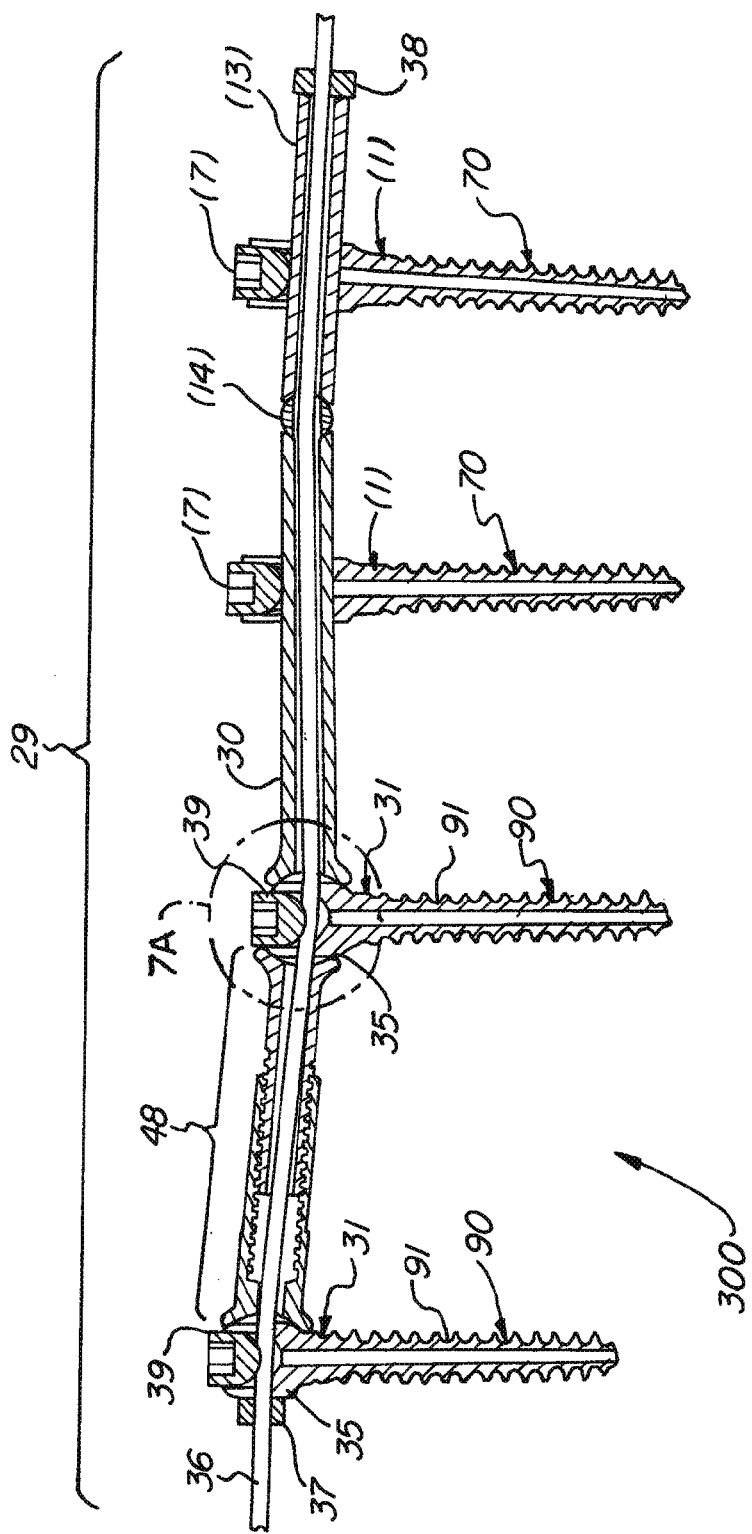
FIG. 7 is a cross-section view of a rod assembly of a spine stabilization system according to the present invention.
Figure 7A:
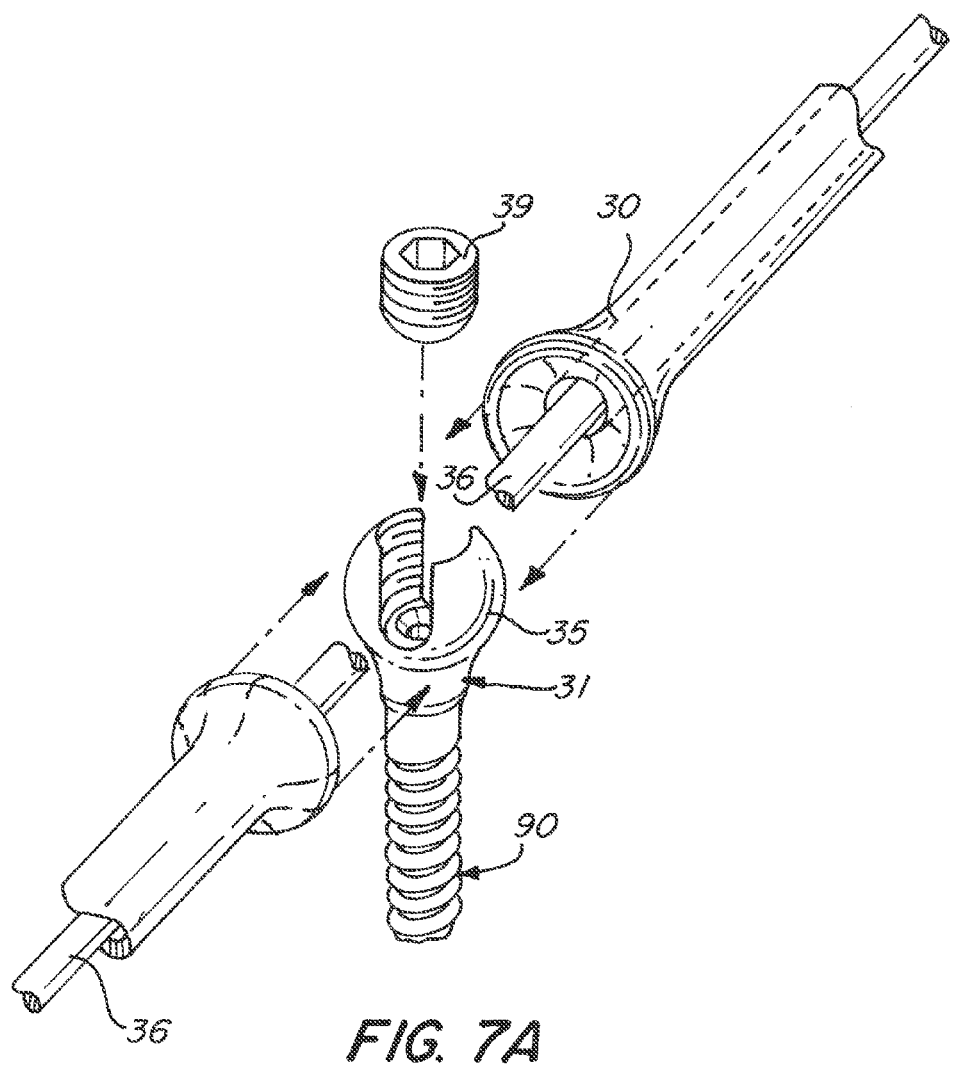
FIG. 7A is an enlarged view of the circled area in FIG. 7.
Figure 8:
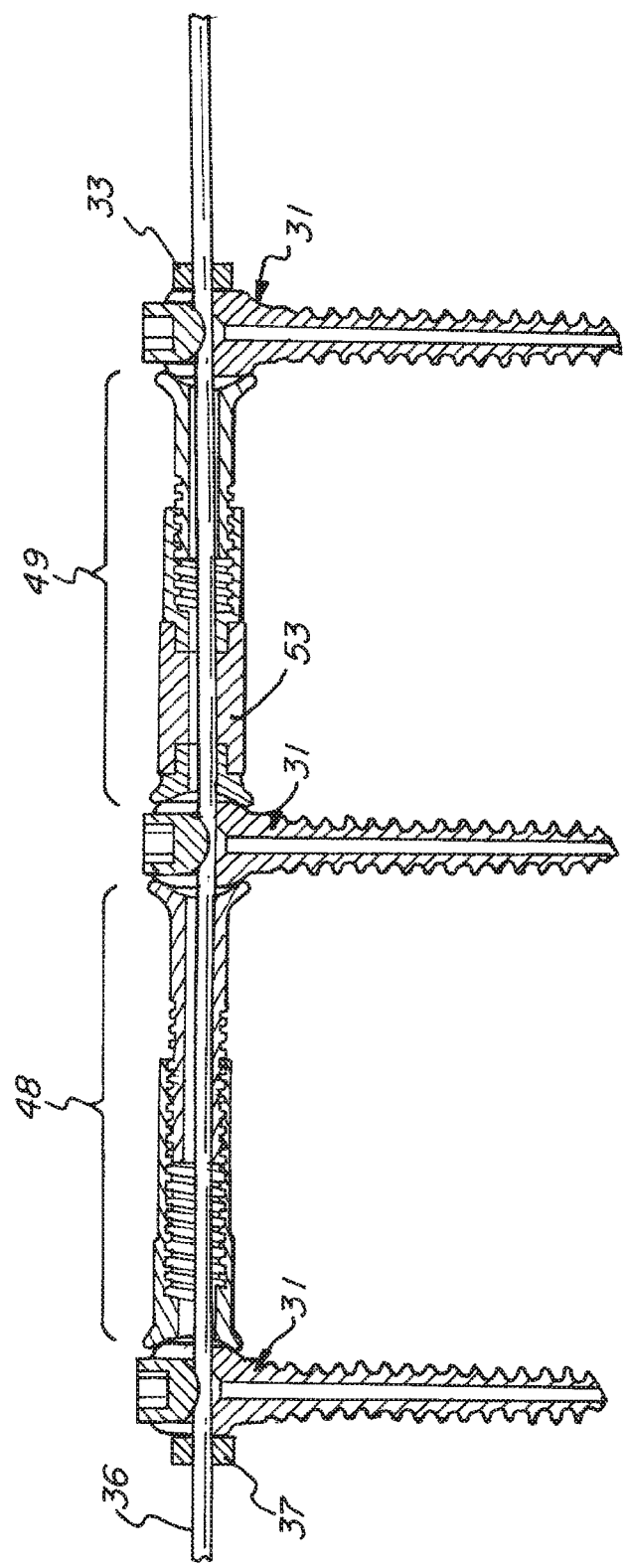
FIG. 8 is a cross-section view of a rod assembly of a spine stabilization system according to the present invention.

FIG. 4A shows that both the rod members 13, 15, and 17 and the articulating positions 14 and 16 have channels 50 shown in the cross-sectional view. Through these channels a tether is fed (not shown in FIG. 4). A tether is shown in FIGS. 7 and 8. It is necessary for the channels 50 of each component to be aligned sufficiently such that a tether can be fed through from one end of rod assembly 28 to the other end of rod assembly 28. FIG. 4A also clearly shows the round end surfaces of the rod members 13, 15, and 17.

Figure 5:
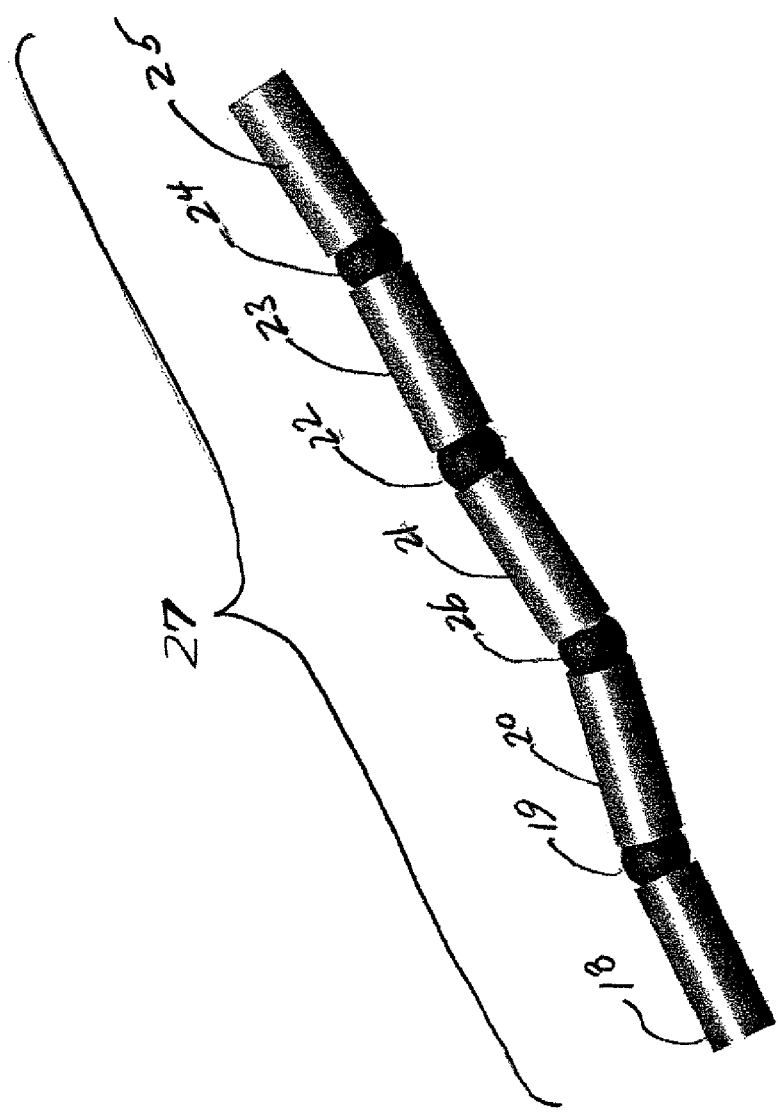
FIG. 5 is a perspective view of a rod assembly of one of the spine stabilization systems of FIG. 1.

If a greater degree of freedom, i.e. more articulation, is necessary or desired to align the rod members with the bone anchor assemblies, it is beneficial to increase the number of pivot members within the rod assembly. FIG. 5 shows that the number of pivot members can be increased over a given total length of the rod assembly. Rod assembly 27 as shown in FIG. 5 is substantially the same length as rod assembly 28 as shown in FIG. 4. Rod assembly 27, however, has four pivot members 19, 26, 22, and 24 disposed between rod members 18, 20, 21, 23, and 25. A greater number of pivot members for a fixed total length of the rod assembly means that the length of the rod members 13, 15, 17, 18, 20, 21, 23, 25 are decreased. The number of pivot members and rod numbers, as well as the length of the rod members is varied to account for differing situations. Rod members of varying lengths are included in a single rod assembly according to some embodiments of the invention.

Figure 6:
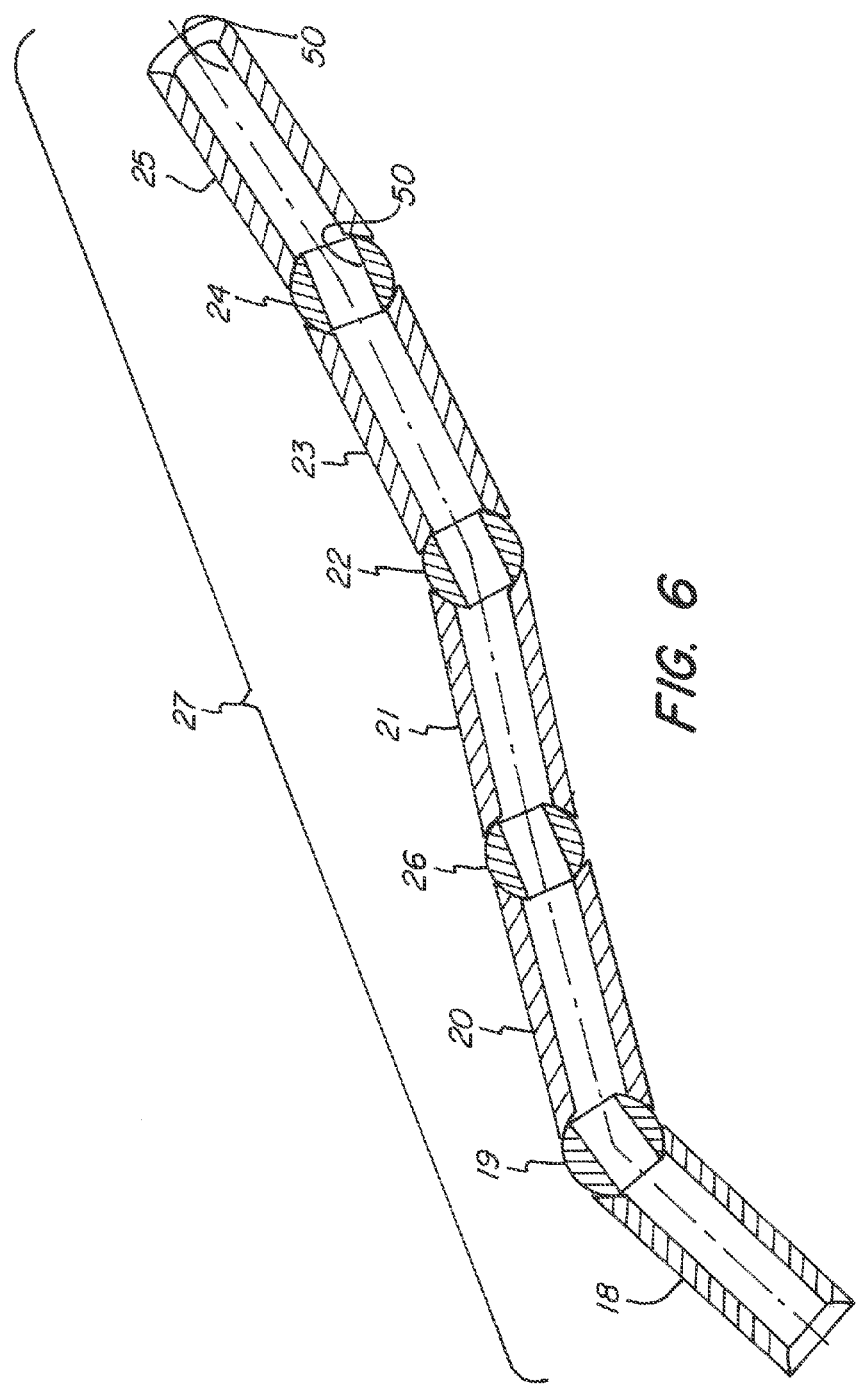
FIG. 6 is a cross-section view of the rod assembly of FIG. 5.

FIG. 6 shows a cross-sectional view of rod assembly 27. The pivot members 19, 26, 22, and 24 and rod members 18, 20, 21, 23, and 25 are shown with channels 50, also for receipt of a tether such as that shown in FIGS. 7 and 8.

FIG. 7 shows spine stabilization system 300, which is an alternative embodiment of the present invention. Spine stabilization system 300 includes rod assembly 29, bone anchor assemblies 70, tether 36, and bone screw assemblies 90. In this embodiment, rod assembly 29 has rod member 13 which articulates about pivot member 14, as before, but also has rod member 30 which articulates about both the pivot member 14 and the upper rounded portion 35 of the screw shaft member 31 of bone screw assembly 90. Rod assembly 29 also includes adjustable rod member 48. Bone screw assemblies 90 include a screw shaft member 31 and a screw head member 39. The screw shaft members 31 have a lower portion 91 for inserting into bone tissue and an upper portion 35. The upper rounded portion 35 has a substantially round shape such that it will interface with the substantially round end surface of rod member 30 and the substantially round end surface of adjustable rod member 48. Rod member 30 is thus capable of articulation about the upper rounded portion 35 of the screw shaft member 31. Thus, it is also possible to have a series of individual rods that articulate about the region of the bone screw heads.

FIG. 7 shows that the ends of rod member 30 have different round end surfaces to account for the different sizes of the pivot member 14 and the upper rounded portion 35. In some embodiments, however, the pivot members and the upper rounded portions of the screw shaft members have substantially similar shapes, so that a single round end surface is present on both ends of the rod members used in the rod assembly.

The tether 36 runs through the channels formed in the components of rod assembly 300. It is anchored at either end of the rod assembly 300 by stoppers 37 and 38. The tension of the tether 36 along the length of rod assembly 300 can be further adjusted by the screw head members 39. Screw head members 39 have threads on their outer surfaces which engage corresponding threads on the upper rounded portions 35 so as to be capable of clamping down on tether 36. In some embodiments, the screw head members further include a small protrusion on their lower surfaces that pierces the tether 36 so as to more effectively lock it into place. In other embodiments, the tether 36 is not anchored by all of the bone screw assemblies. In such a case, a bone screw assembly comprises only the screw shaft member which has a hole formed in the upper rounded portion 35 for receiving the tether 36. In such a case, a screw head member 39 is not used to anchor the tether 36, and the tether 36 is permitted to move relative to the bone screw assembly.

The tether 36 is formed of a material having a selected amount of elasticity, depending on the degree of movement and articulation that is desired in the system. For rigid fixation systems, the tether material has a very low elasticity.

Figure 9:
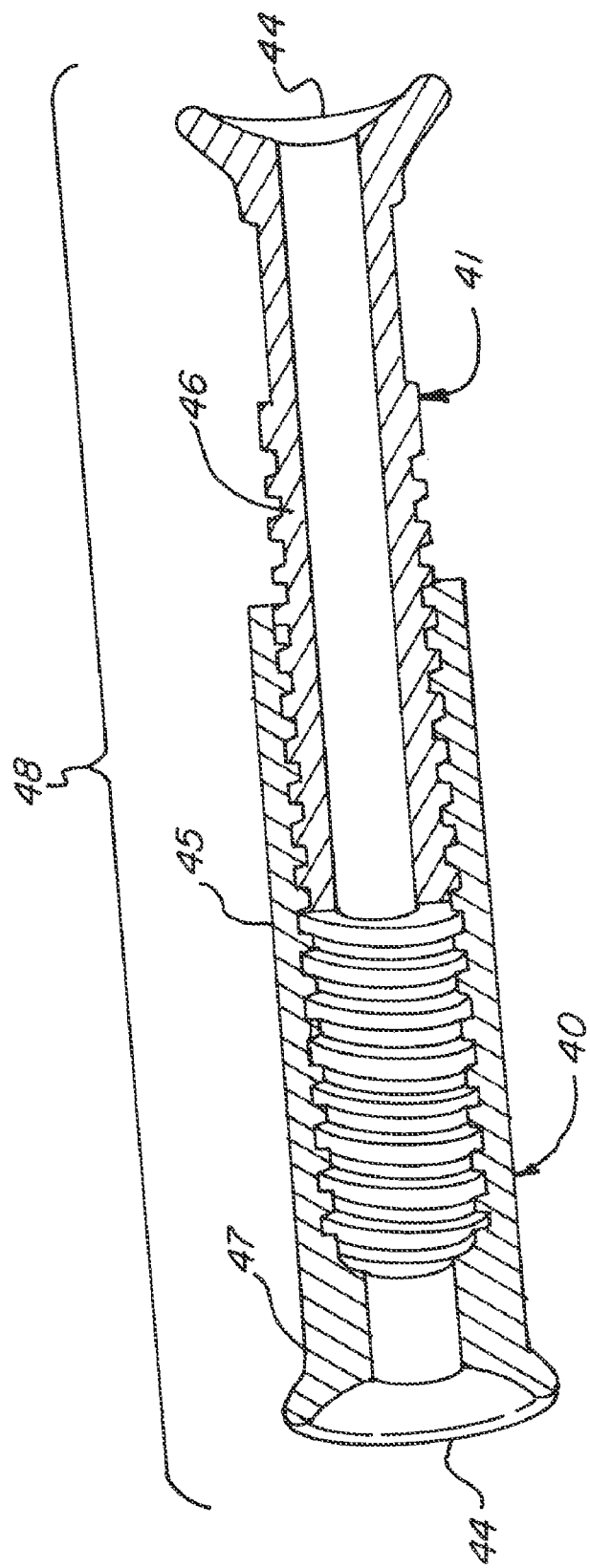
FIG. 9 is a perspective view of an adjustable rod member of a rod assembly of the spine stabilization system of FIG. 7.
Figure 9A:
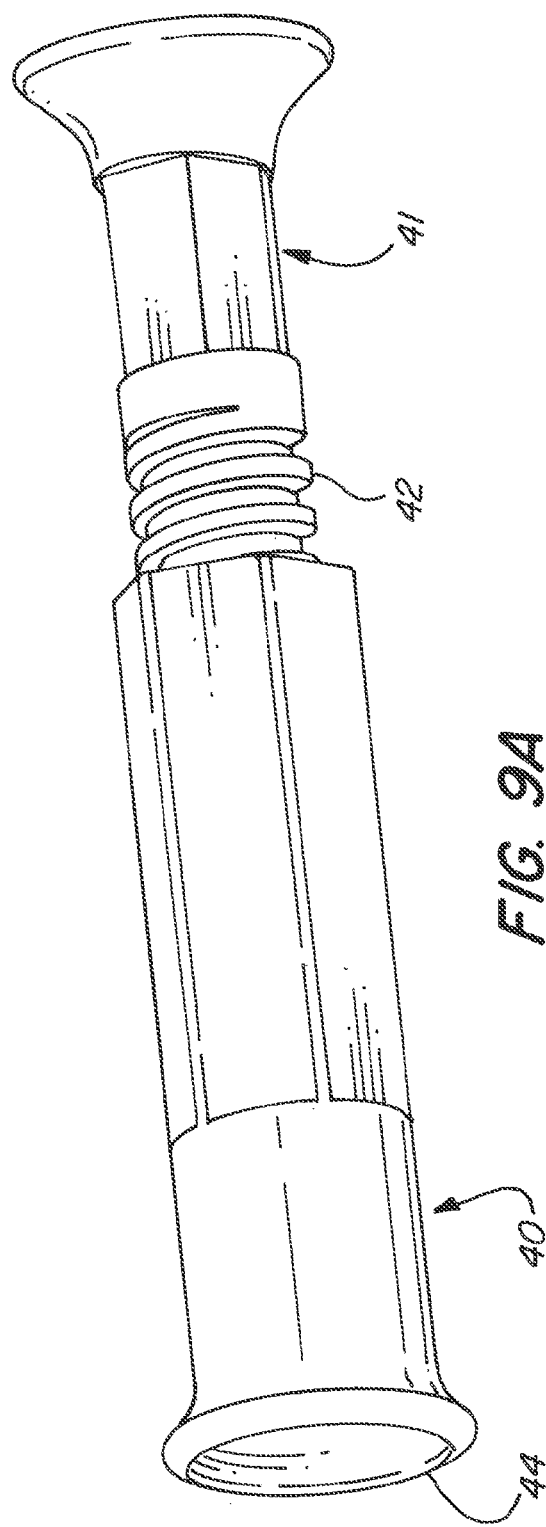
FIG. 9A is a cross-section view of the adjustable rod member of FIG. 9.

FIG. 7 also shows adjustable rod member 48, disposed and articulating between two bone screw assemblies 90. FIG. 9 shows a cross-sectional view of the adjustable rod member 48. FIG. 9A shows a close up view of the adjustable rod member 48. The adjustable rod member 48 has a first component 41 and a second component 40, each having an end with a substantially round end surface. First component 41 has channel 46 along its axis and threads 42 formed on its outer surface. Second component 40 has channel 47 along its axis and threads 45 formed on its inner surface. The length of adjustable rod member 48 may be easily adjusted by rotating the first component 41 and the second component 40 relative to one another. The first component 41 and the second component 40 will move in a telescopic-like motion relative to one another. This means that it is possible to have a universal rod member that is capable of being utilized for different pedicle screw displacements. The adjusting feature also enables the necessary rod member length to be accurately determined.

Use of the adjustable rod member further eases installation of spine stabilization systems according to the present invention. Errors in the measurement or calculation of the distance between bone anchors are easily corrected for by simple rotation of the adjustable rod member prior to its installation. It also allows adjustments to be made during surgery after the adjustable rods have been installed between bone anchors.

Figure 11:
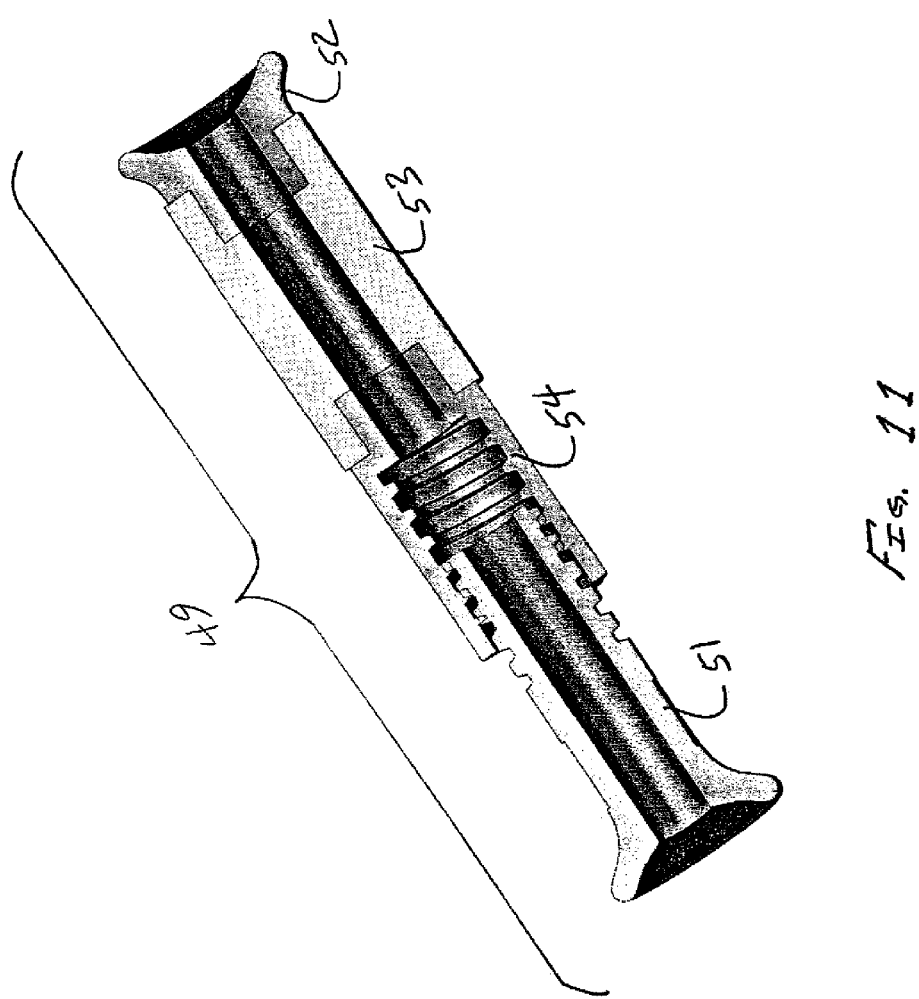
FIG. 11 is a cross-section of an adjustable rod member with an elastomeric element of the rod assembly of FIG. 10.

A further embodiment is shown in FIG. 8, which shows a spine stabilization system such as those already described but including a further refinement. FIG. 8 shows adjustable rod member 49 with an elastomeric element 53 included. FIG. 10 shows a close up view of the rod member 49 and FIG. 11 shows a cross-sectional view of rod member 49. Rod member 49 incorporates elastomeric element 53 into the second component 54. Inclusion of such an elastomeric element is effective for dynamic stabilization since it allows the rod member 49 to expand or contract along its axis. The extent of the allowable motion is variable based on the size of the elastomeric element and the material out of which it is formed. The extent of allowable motion is also variable according to the number of rod members which include an elastomeric element. The elastomeric component is designed to be integrated into the body of the first component. The elastomeric component also has a channel at the core of the elastomeric component that aligns with the channel formed in the proximal end 52 and distal end 54 of the first component. In some embodiments, an elastomeric component is included in non-adjustable rod members, such as rod members 13, 15, 17, 18, 20, 21, 23, and 25, in a similar fashion.

The elastomeric element, whether present in non-adjustable or adjustable rod members, permits the surgeon to create a dynamic stabilization system from a fixed stabilization system. The elastomeric element allows for a selected degree of both linear and non-linear movement. As stated above, the elastomeric element allows for movement along the axis of the rod member. Additionally, the elastomeric member allows for a bending movement or a twisting movement within the rod member.

The dynamic stabilization system enables orthopedic fixation to be controlled by a different combination of rod elements to provide a varied range of motion between adjacent vertebrae as well as specific flexibility between the adjacent vertebrae or levels. The surgeon can make intra-operative adjustments from rigid fixation to dynamic stabilization and where desired also provide 'soft-stabilization' or 'micro motion'. Clearly, the present invention is used for fixed stabilization as well as for dynamic stabilization.

Specifically left and right rigid connecting rods between vertebrae would be replaced with the dynamic, flexible assembly which includes a elastomeric element that provides for linear or non-linear compression. The compressive load at rest and the load under spinal extension (backward bending) would depend on the choice of biocompatible elastomeric materials and the associated durometer and compressive or spring properties of the element.

The flexion forces (forward bending) can also be adjusted and balanced against the extension forces by tensioning the tether between the specific vertebrae. The amount of compression in the element and the amount of the counteracting flexion forces (or tensile forces) in the tether would also determine the range of motion in or across the interbody by using force to control displacement between the vertebrae. The surgeon would have the intra-operative choice to tailor the dynamic properties to best fit the needs of the patient.

A benefit of the present invention is that different elements can be mixed and matched and used to construct an overall system from a rigid fixed system to a dynamic system. FIGS. 7 and 8 present examples of how the different types of rods described above can be simultaneously incorporated to form an overall spine stabilization system.

Although the invention has been described with reference to a particular arrangement of parts, features, and the like, these are not intended to exhaust all possible arrangements or features, and indeed many modifications and variations will be ascertainable to those of skill in the art.

What is claimed is:

1. A spine stabilization system, comprising:
   a rod assembly, comprising:
     a plurality of rod members, each rod member having a length and comprising a first end and a second end, wherein each of the first end and the second end has a substantially round end surface oriented in the direction of an axis of the at least one rod member, and each rod member has an axial channel along its length;
     at least one substantially round pivot member which is disposed between rod members and which makes substantially flush contact with the round end surfaces of the rod members and which has a channel;
     a tether disposed in the axial channels of the rod members and the channel of the at least one substantially round pivot member;
   at least two bone anchor assemblies, each bone anchor assembly comprising:
     an anchor member comprising a lower rod portion for insertion into bone tissue and an upper portion, wherein the upper portion is adapted to receive a portion of a rod member and has an inner threaded surface;
a screw top member having an outer threaded surface for engaging with the inner threaded surface of the upper portion of the anchor member; and
wherein the bone anchor assemblies hold the rod assembly between the screw top member and the upper portion of the anchor member;
at least one bone screw assembly, comprising:
a screw shaft member comprising a lower portion for inserting into bone tissue and an upper rounded portion adapted to interface with the substantially round end surface of at least one rod member, and wherein the upper rounded portion has a threaded inner cylindrical surface;
a screw head member receivable within the upper rounded portion of the screw shaft member, wherein the screw head member includes threads on an outer surface thereof designed to engage the threads on the inner cylindrical surface of the upper rounded portion of the screw shaft member;
wherein the at least one bone screw assembly is disposed at the end of at least one rod member of the rod assembly such that the tether may be anchored in place between the screw shaft member and the screw head member, thereby connecting the at least one bone screw assembly and the rod assembly.

2. The spine stabilization system of claim 1, wherein the rod assembly further comprises at least one adjustable rod member, comprising:
a first component comprising a first end with a substantially round end surface oriented in the direction of an axis of the at least one rod member, a second end, an axial channel for receiving the tether, and threads on an outer surface of the first component adjacent to the second end;
a second component comprising a first end, a second end with a substantially round end surface oriented in the direction of an axis of the at least one rod member, an axial channel for receiving the tether, and threads adjacent to the first end on an inner surface of the axial channel; and
wherein the threads of the first component are capable of engaging with the threads of the second component so as to form a rod member of a first length;
wherein the first component may be rotated relative to the second component such that the threads draw the first component closer to the second component and form a rod member of a second length.

3. The spine stabilization system of claim 2, wherein the second component further comprises an elastomeric element disposed between the first end and the second end of the second component.

4. The spine stabilization system of claim 1, wherein the tether is formed of an elastomeric material.

5. The spine stabilization system of claim 1, wherein at least one substantially round pivot member is formed of an elastomeric material.

6. The spine stabilization system of claim 1, wherein the rod members having varying lengths.

7. The spine stabilization system of claim 1, wherein the rod assembly includes at least one rod member comprising an elastomeric element disposed between the first end and the second end of the rod member.

8. The spine stabilization system of claim 1, wherein the rod assembly includes tether anchor members for preventing movement of the tether relative to the other components of the rod assembly.

9. A spine stabilization system, comprising:
a rod assembly, comprising:
a plurality of rod members, each rod member having a length and comprising a first end and a second end, wherein each of the first end and the second end has a substantially round end surface oriented in the direction of an axis of the at least one rod member, and each rod member has an axial channel along its length;
at least one substantially round pivot member which is disposed between rod members and which makes substantially flush contact with the round end surfaces of the rod members and which has a channel;
a tether disposed in the axial channels of the rod members and the channel of the at least one substantially round pivot member;
at least two bone anchor assemblies, each bone anchor assembly comprising:
an anchor member comprising a lower rod portion for insertion into bone tissue and an upper portion, wherein the upper portion is adapted to receive a portion of a rod member and has an inner threaded surface;
a screw top member having an outer threaded surface for engaging with the inner threaded surface of the upper portion of the anchor member; and
wherein the bone anchor assemblies hold the rod assembly between the screw top member and the upper portion of the anchor member;
at least one bone screw assembly, comprising:
a screw shaft member comprising a lower portion for inserting into bone tissue and an upper rounded portion adapted to interface with the substantially round end surface of at least one rod member, and wherein the upper rounded portion has a threaded inner cylindrical surface;
a screw head member receivable within the upper rounded portion of the screw shaft member, wherein the screw head member includes threads on an outer surface thereof designed to engage the threads on the inner cylindrical surface of the upper rounded portion of the screw shaft member;
wherein the at least one bone screw assembly is disposed at the end of at least one rod member of the rod assembly such that the tether may be anchored in place between the screw shaft member and the screw head member, thereby connecting the at least one bone screw assembly and the rod assembly,
wherein the screw head member contacts the tether and presses the tether against the screw shaft member.

10. The spine stabilization system of claim 9, wherein the screw head member includes a protrusion on its lower surface which pierces the tether.

11. A spine stabilization system, comprising:
a rod assembly, comprising:
at least one rod member having a length and comprising a first end and a second end, wherein at least one of the first end and the second end has a substantially round end surface oriented in the direction of an axis of the at least one rod member, and the at least one rod member has an axial channel along its length;
a tether disposed in the axial channel;
at least two bone screw assemblies, wherein at least one of said bone screw assemblies comprises:

a screw shaft member comprising a lower portion for inserting into bone tissue and an upper rounded portion adapted to interface with the substantially round end surface of the at least one rod member; and wherein the bone screw assemblies are disposed at the end of the at least one rod member of the rod assembly such that the tether connects the bone screw assemblies and the rod assembly.

12. The spine stabilization system of claim 11, wherein the rod assembly further comprises at least one adjustable rod member, comprising:
a first component comprising a first end with a substantially round end surface oriented in the direction of an axis of the at least one rod member, a second end, an axial channel for receiving the tether, and threads on an outer surface of the first component adjacent to the second end;
a second component comprising a first end, a second end with a substantially round end surface oriented in the direction of an axis of the at least one rod member, an axial channel for receiving the tether, and threads adjacent to the first end on an inner surface of the axial channel; and
wherein the threads of the first component engage with the threads of the second component such that the overall length of the adjustable rod member may be adjusted.

13. The spine stabilization system of claim 12, wherein the second component further comprises an elastomeric element disposed between the first end and the second end of the second component.

14. The spine stabilization system of claim 11, wherein the tether is formed of an elastomeric material.

15. The spine stabilization system of claim 11, wherein the rod assembly comprises a plurality of the rod members.

16. The spine stabilization system of claim 15, wherein the rod members have varying lengths.

17. The spine stabilization system of claim 15, wherein the rod assembly further comprises at least one substantially round pivot member which is disposed between rod members and has a channel in which the tether is disposed so as to connect the at least one substantially round pivot member with the rod members.

18. The spine stabilization system of claim 17, wherein at least one of the substantially round pivot members is formed of an elastomeric material.

19. The spine stabilization system of claim 11, wherein the spine stabilization system further comprises at least one bone anchor assembly which comprises an anchor member and a screw top member for attaching between the first end and the second end of a rod member.

20. The spine stabilization system of claim 11, wherein the rod assembly includes at least one rod member comprising an elastomeric element disposed between the first end and the second end of the rod member.

21. The A spine stabilization system, comprising:
a rod assembly, comprising:
at least one rod member having a length and comprising a first end and a second end, wherein at least one of the first end and the second end has a substantially round end surface oriented in the direction of an axis of the at least one rod member, and the at least one rod member has an axial channel along its length;
a tether disposed in the axial channel;
at least two bone screw assemblies, wherein at least one of said bone screw assemblies comprises:
a screw shaft member comprising a lower portion for inserting into bone tissue and an upper rounded portion adapted to interface with the substantially round end surface of the at least one rod member; and wherein the bone screw assemblies are disposed at the end of the at least one rod member of the rod assembly such that the tether connects the bone screw assemblies and the rod assembly, wherein at least one of said bone screw assemblies further comprises:
that the upper rounded portion of the screw shaft member has a threaded inner cylindrical surface;
a screw head member receivable within the upper rounded portion of the screw shaft member, wherein the screw head member includes threads on an outer surface thereof designed to engage the threads on the inner cylindrical surface of the upper rounded portion of the screw shaft member; and
wherein the screw head member contacts the tether and presses the tether against the screw shaft member so as to anchor the tether in place between the screw shaft member and the screw head member.

22. The spine stabilization system of claim 21, wherein the screw head member includes a protrusion on its lower surface which pierces the tether.

23. A spine stabilization system, comprising:
a rod assembly, comprising:
one or more elongated rod members wherein each elongated rod member comprises a channel extending along its longest dimension and a first end and a second end both having a substantially round end surface oriented in the direction of an axis of the at least one rod member;
at least one adjustable rod member comprising:
a first component comprising a first end with a substantially round end surface oriented in the direction of an axis of the at least one rod member, a second end, an axial channel, and threads on an outer surface of the first component adjacent to the second end;
a second component comprising a first end, a second end with a substantially round end surface oriented in the direction of an axis of the at least one rod member, an axial channel, and threads adjacent to the first end on an inner surface of the axial channel; and
wherein the threads of the first component engage with the threads of the second component such that the overall length of the adjustable rod member may be adjusted; and
a tether disposed in the channels of the elongated rod members and the adjustable rod members and linking the elongated rod members and the adjustable rod members together;
a plurality of bone screw assemblies, which are disposed between the elongated rod members and the adjustable rod members of the rod assembly, wherein at least one bone screw assembly comprises:
a screw shaft member comprising a lower portion for inserting into bone tissue and an upper rounded portion adapted to interface with the substantially round end surfaces of the elongated rod members and the adjustable rod members.

24. The spine stabilization system of claim 23, wherein at least one bone screw assembly further comprises:
that the upper rounded portion of the screw shaft member has a threaded inner cylindrical surface; and
a screw head member receivable in the upper rounded portion of the screw shaft member, comprising a threaded outer surface for engaging with the threaded inner cylindrical surface of the upper rounded portion and which contacts the tether of the rod assembly to substantially prevent movement of the tether relative to the bone screw assembly.

25. The spine stabilization system of claim 24, wherein the screw head member has a protrusion on a lower surface which pierces the tether.

26. The spine stabilization system of claim 23, wherein the tether is formed of an elastomeric material.

27. The spine stabilization system of claim 23, wherein at least one second component of the at least one adjustable rod member further comprises an elastomeric element disposed between the first end and the second end of the second component.

28. The spine stabilization system of claim 23, wherein the rod assembly comprises a plurality of the elongated rod members.

29. The spine stabilization system of claim 28, wherein the elongated rod members have varying lengths.

30. The spine stabilization system of claim 28, wherein the rod assembly further comprises at least one substantially round pivot member which is disposed between the elongated rod members and the adjustable rod members and has a channel in which the tether is disposed so as to connect the at least one substantially round pivot member with the elongated rod members and the adjustable rod members.

31. The spine stabilization system of claim 30, wherein at least one substantially round pivot member is formed of an elastomeric material.

32. The spine stabilization system of claim 23, wherein the spine stabilization system further comprises at least one bone anchor assembly which comprises an anchor member and a screw top member for attaching between the first end and the second end of an elongated rod member.

33. A spine stabilization system, comprising:
a rod assembly, comprising:
    a plurality of adjustable rod members, each adjustable rod member comprising:
        a first component comprising a first end with a substantially round end surface oriented in the direction of an axis of the at least one rod member, a second end, an axial channel, and threads on an outer surface of the first component adjacent to the second end;
        a second component comprising a first end, a second end with a substantially round end surface oriented in the direction of an axis of the at least one rod member, an axial channel, and threads adjacent to the first end on an inner surface of the axial channel; and
        wherein the threads of the first component engage with the threads of the second component such that the overall length of the adjustable rod member may be adjusted; and
    at least one substantially round pivot member having a channel and being disposed between two adjustable rod members such that an outer surface of the at least one substantially round pivot member is in substantially flush contact with the substantially round end surfaces of the adjustable rod members and such that the channel of the at least one substantially round pivot member is aligned with the axial channels of the adjustable rod members;
    a tether passing through the channels of the at least one substantially round pivot member and the axial channels of the adjustable rod members;
at least two bone anchor assemblies, each bone anchor assembly comprising:
    an anchor member comprising a lower rod portion for insertion into bone tissue and an upper portion, wherein the upper portion is adapted to receive a portion of a rod member and has an inner threaded surface;
    a screw top member having an outer threaded surface for engaging with the inner threaded surface of the upper portion of the anchor member; and
    wherein the rod assembly is secured between the anchor members and the screw top members of the bone anchor assemblies.

34. The spine stabilization apparatus of claim 33, wherein the tether is formed of an elastomeric material.

35. The spine stabilization apparatus of claim 33, wherein at least one substantially round pivot member is formed of an elastomeric material.

36. The spine stabilization system of claim 33, wherein the spine stabilization system further comprises at least one bone screw assembly, comprising:
    a screw shaft member comprising a lower portion for inserting into bone tissue and an upper rounded portion adapted to interface with the substantially round end surface of at least one adjustable rod member, and wherein the upper rounded portion has a threaded inner cylindrical surface;
    a screw head member receivable within the upper rounded portion of the screw shaft member, wherein the screw head member includes threads on an outer surface thereof designed to engage the threads on the inner cylindrical surface of the upper rounded portion of the screw shaft member;
wherein the at least one bone screw assembly is disposed at the end of at least one adjustable rod member of the rod assembly such that the tether may be anchored in place between the screw shaft member and the screw head member, thereby connecting the at least one bone screw assembly and the rod assembly.

37. The spine stabilization apparatus of claim 33, wherein at least one second component of an adjustable rod member further comprises an elastomeric element disposed between the first end and the second end of the second component.

38. An adjustable rod member for use in a spine stabilization system, comprising:
    a first component comprising a first end with a substantially round end surface oriented in the direction of an axis of the at least one rod member, a second end, an axial channel, and threads on an outer surface of the first component adjacent to the second end;
    a second component comprising a first end, a second end with a substantially round end surface oriented in the direction of an axis of the at least one rod member, an axial channel, an elastomeric element disposed between the first end and the second end, and threads adjacent to the first end on an inner surface of the axial channel; and
    wherein the threads of the first component engage with the threads of the second component such that the overall length of the adjustable rod member may be adjusted.

* * * * *